(12) United States Patent
Gastonguay et al.

(10) Patent No.: US 8,298,582 B2
(45) Date of Patent: Oct. 30, 2012

(54) POLYSACCHARIDE-BASED IMPREGNATED SOLID MATERIAL WITH IMPROVED STABILITY, PROCESSES FOR THE PREPARATION THEREOF AND IMPREGNATING SOLUTIONS USED

(75) Inventors: Louis Gastonguay, Varennes (CA);
Michel Perrier, Montréal (CA);
Paul-Étienne Harvey, Saint-Hubert (CA); Jean-François Labrecque, Montréal (CA); Michel Robitaille, Varennes (CA); André Besner, Montréal (CA)

(73) Assignee: Hydro-Quebec, Montreal, Quebec (CA)

( * ) Notice: Subject to any disclaimer, the term of this patent is extended or adjusted under 35 U.S.C. 154(b) by 557 days.

(21) Appl. No.: 12/294,746

(22) PCT Filed: Mar. 28, 2007

(86) PCT No.: PCT/CA2007/000498
§ 371 (c)(1),
(2), (4) Date: Feb. 22, 2010

(87) PCT Pub. No.: WO2007/109898
PCT Pub. Date: Oct. 4, 2007

(65) Prior Publication Data
US 2010/0178358 A1 Jul. 15, 2010

(30) Foreign Application Priority Data
Mar. 28, 2006 (CA) ..................... 2541125

(51) Int. Cl.
*A61K 9/14* (2006.01)
*A61K 51/00* (2006.01)
*A61K 33/42* (2006.01)
*A61K 33/34* (2006.01)
*A61K 33/22* (2006.01)
*A61K 33/36* (2006.01)
*A61K 33/08* (2006.01)
*A01N 59/26* (2006.01)
*A01N 59/22* (2006.01)
*A01N 59/06* (2006.01)
*A01N 59/14* (2006.01)
*A01N 59/20* (2006.01)
*A61M 36/14* (2006.01)

(52) U.S. Cl. ...... 424/488; 424/1.73; 424/1.77; 424/601; 424/622; 424/630; 424/657; 424/667; 424/690; 424/691; 424/724

(58) Field of Classification Search .................. 424/488, 424/1.73, 1.77, 601, 622, 630, 657, 667, 424/690, 691, 724
See application file for complete search history.

(56) References Cited

U.S. PATENT DOCUMENTS

| | | |
|---|---|---|
| 4,076,540 A | 2/1978 | Stossel |
| 4,461,721 A | 7/1984 | Goettsche et al. |
| 4,755,298 A | 7/1988 | Grinstead |
| 5,221,758 A | 6/1993 | Maynard |
| 6,352,583 B1 | 3/2002 | Goettsche et al. |
| 6,365,169 B1 | 4/2002 | Rosenblatt |
| 6,406,749 B1 | 6/2002 | Symons |
| 6,723,352 B2 | 4/2004 | Bosserman |
| 6,844,081 B2 | 1/2005 | Hart et al. |
| 2005/0013939 A1 | 1/2005 | Vinden et al. |

FOREIGN PATENT DOCUMENTS

| | | |
|---|---|---|
| DE | 103 40 093 | 3/2005 |
| EP | 0 361 892 | 4/1990 |
| WO | 91/00327 A1 | 1/1991 |
| WO | WO 98/39146 | 9/1998 |

OTHER PUBLICATIONS

European Search Report dated Aug. 26, 2010, issued in the corresponding European Application No. 07719430.6-2115.
Bizak et al., "Crosslinked Polymer Gels for Boron Extraction Derived Form N-Glucidol-N-Methyl-2 Hydroxypropyl Methacrylate" Marcromol, Chem. Phys., 2000, vol. 201, No. 5, pp. 577-584.
Susan L. Levan, "Chemistry of Fire Retardancy" Advanced in Chemical Series, 207, 1984, pp. 532-574.

Holger Militz, "Thermal Treatment of Wood: European Processes and Their Background" The International Research Group on Wood Preservation 33$^{rd}$ Annual Meeting, 2002, 20 pages.

M.R. Powell, "Treatment of Wood with Royale Stabilising Oil" European Conference on Wood Modification, 2003, 8 pages.

Robert H. White, "Flame Retardancy of Wood: Present Status, Recent Problems, and Future Fields" Recent Advances in Flame Retardancy of Polymeric Materials: Proceedings of 3rd Annual BCC Conference on Flame Retardance, 1992, pp. 250-257.

Yoshimura et al., "Complexation of Boric Acid with the N-Methyl-D-Glucamine Group in Solution and in Crosslinked Polymer" J. Chem. Soc., Faraday Trans., 1998, vol. 94, No. 5, pp. 683-689.

Book of Standards 2006, of the American Wood-Preservers' Association Standard, Section P5-06, pp. 111-116.

International Search Report (PCT/ISA/210), Jun. 26, 2007.

*Primary Examiner* — Richard Schnizer
*Assistant Examiner* — Jane C Osweckt

(74) *Attorney, Agent, or Firm* — Buchanan Ingersoll

(57) ABSTRACT

A polysaccharide-based solid material including, in its mass, at least one active agent having bactericidal, fungal, insecticidal and/or flame-retardant properties, and at least one complexing agent and/or at least one polymeric matrix having a complexing agent. The active agent includes at least one compound selected from the group including boron, silica, aluminum, phosphorus, iodine, derivatives thereof, aluminosilicate derivatives, and mixtures thereof. The solid material is characterized by an improved stability and by reduced environmental impact, and makes it possible to prepare materials based on wood particles and woods having a particular resistance against environmental attacks such as moisture.

8 Claims, 4 Drawing Sheets

POLYSACCHARIDE-BASED IMPREGNATED SOLID MATERIAL WITH IMPROVED STABILITY, PROCESSES FOR THE PREPARATION THEREOF AND IMPREGNATING SOLUTIONS USED

FIELD OF THE INVENTION

The invention relates to a polysaccharide-based solid material comprising, in its mass, at least one active agent which has bactericidal and/or fungal and/or insecticidal properties and/or properties as a flame retardant, and at least one complexing agent and/or at least one polymeric matrix comprising a complexing agent.

The active agent selected consists mainly of one or more environmentally friendly compounds.

The complexing agent selected has the property of being able to complex bactericidal and/or fungal and/or insecticidal and/or flame-retardant compounds present in the solid material. The solid material of the invention is characterized by an improved stability and by a reduced environmental impact.

The invention also relates to the processes implemented in order to carry out the impregnation of the polysaccharide-based solid material, and also to the impregnating solutions used for this purpose.

The invention makes it possible in particular to prepare materials based on wood particles and woods which exhibit a particular resistance, in particular against the environmental attacks to which these materials are exposed when used in the open air, and more particularly when used in atmospheres with a high moisture content, characteristic in particular of subtropical or tropical climates.

The invention also relates to the objects prepared using, as constituent material, at least one of the polysaccharide-based solid materials of the invention. The use of these objects has a minimum impact on the environment, since it avoids the release of highly toxic chemical compounds into the environment.

RELATED ART

The microbiological degradation of lignocellulose is one of the most important natural phenomena. Fungal activity is necessary in order to enable effective reuse of the biomass, but it considerably limits the use of wood by impairing its density and its mechanical strength. In the past, methods have been developed for the purpose of preventing, or even eradicating, wood-eating fungi.

However, these conventional methods of impregnating wood are based on the use of not insignificant amounts of toxic agents such as creosote, chlorinated phenols or copper-based, chromium-based and arsenic-based inorganic salts.

The increasingly severe restrictions that have been brought in for the use of environmentally toxic substances, and also the not insignificant dangers that they represent for the health and safety of people who may come into contact with these products, greatly reduce the value of these methods and lead to anticipate that they will be prohibited in the more or less long term.

Attempts have more recently been made to improve the resistance of wood to bacterial and fungal agents naturally present in nature, by incorporating therein agents that are not aggressive with respect to the environment, such as boron, in the form of boric acid, or of borax, which are agents that are recognized for their preserving agent properties and for the fact that they are environmentally well tolerated.

Thus, the U.S. Pat. No. 6,365,169 (Rosenblatt), granted on 2 Apr. 2002, describes a form of controlled and continuous release of iodine by means of a complex of a polyvinyl alcohol (PVA) starch and iodine, characterized by the PVA-based coating being insoluble in boiling water. The polyvinyl alcohol is present in the form of a coating reacting with various types of non-mineral acids containing catalysts/curing or insolubilizing agents deposited on a cellulose substrate or on other substrates and subsequently complexed with iodine. These sponges constitute a solid antimicrobial device which releases controlled amounts of iodine on contact sufficient to kill microorganisms, and leaves minimal residues.

The U.S. Pat. No. 6,406,749 (Symons), granted on 18 Jun. 2002, describes a process for the chemical modification of wood which consists in impregnating the wood, under vacuum, with ammonia gas. After removal of the gas residue, and while still under pressure, the ammonia-impregnated wood is impregnated with an impregnating composition containing dicarboxylic or tricarboxylic anhydride, polyvinyl alcohols, partially or fully saponified, and water. The impregnating composition may also, and preferably, include a water-soluble boron compound. In addition to the fact that the very structure of the wood is affected by the first ammonia-treatment step, the presence of anhydrides results in a modification of the wood in the presence of polyvinyl alcohol, so as to form a hexamethylenetetramine-based resin, which is a formaldehyde donor, formaldehyde being a chemical compound recognized for its toxicity, in particular as a carcinogenic agent.

The U.S. Pat. No. 6,723,352 (Bosserman), granted on 20 Apr. 2004, describes a method for producing products for treating wood and other cellulose products in order to improve the flame retardancy and the insecticidal and fungal properties of said products. A calcium borate ore, such as a colemanite, is reacted first with an acid such as acetic acid. The reaction products, including calcium in solution, are then treated with aqueous ammonia, and produce an ammonium pentaborate. The resulting solution is applied to the wood or other cellulose products by methods such as pressure, diffusion, or immersion and/or dipping treatment. The products have higher leach resistance when compared with compounds used in conventional treatments. This method necessarily involves the presence of a solution containing the calcium-based mineral filler and does not involve any complexation of the boron with a complexing agent.

The studies by Hart et al. presented in U.S. Pat. No. 6,844,081, granted on 18 Jan. 2005, describe the application of boric acid in the presence of a metallocene catalyst and a free-radical initiator which reacts in the wood in order to form crosslinking between the cellulose fibres and the boric acid. This network is subsequently coated with a sealing film in order to protect the protective agent against bad weather. This technique proves to be complex due to the fact that it necessarily requires the use of a second polymer.

United States patent application US-A1-2005/0013939 (Vinden et al.), published on 20 Jan. 2005, describes a method for modifying the solubility of a boron compound (trimethyl borate) by allowing it to react with the moisture in the wood. This technique, which requires the use of methanol, which is a highly inflammable compound, for the impregnation with trimethyl borate, generates risks of fire and even explosion.

During the first European Conference on Wood Modification (ECWM 2003), which was held in April 2003 in Ghent in Belgium, various methods for modifying wood were mentioned. The hydroxyl groups present on the cell walls of wood are responsible for several physical and chemical properties of wood. In particular, they play an important role in the biological degradation and/or the physical process which allows absorption and desorption of water. Any alteration of these functions may have a considerable impact on the hydrophilicity of the wood. It will also have an impact on the recognition of the components of the wood by the enzymes of the rotting fungi responsible for the digestion of the wood and its conversion to sugars.

The hydroxyl functions of wood can be altered by a considerable number of chemical modification processes. Among the very many possibilities of reactions that may be involved, mention may be made of the following: formation of ethers, addition of an acetal or of a carbonyl function, esterification, formation of urethanes, oligoesterification (combination of more than one reaction), chemical oxidation, silylation, acetylation, furfurylation and formation of a melamine-formaldehyde resin.

Thermal modifications may be added to these chemical modifications. They involve a thermal treatment of the wood, normally accompanied by impregnation of oil into the wood. By applying heat, certain functions of the wood polymers are cleaved and new hydrophobic functions are permanently formed.

The Menz Holz OHT (Oil-Heat Treatment) process, described by H. Militz in Thermal Treatment of Wood: European Process and their background, IRG $33^{rd}$ Annual meeting, is intended to improve the lifespan of outdoor wood not in contact with the soil, and it is carried out in a closed chamber. After the wood load has been placed in a sealed reservoir, a hot oil is added and then kept at high temperature (180-220° C.) in order to impregnate the wood. In order for the treatment to be effective and for the chemical modifications to take place, it is necessary to maintain the temperature at the heart of the sample for more than 2 hours (normally between 2 and 4 hours).

The process called Osmose Royale Process, described by Powell in Powell M. R. (2003); European Conference on Wood Modification, the purpose of which is also to improve the lifespan of outdoor wood, is carried out at lower temperature (60-90° C.) in order to prevent chemical modifications and simply in order to allow impregnation of the wood with oil. The aim of this treatment is to make it possible to obtain a wood with a low moisture content. A vacuum subsequent to the impregnation makes it possible to remove the excess surface oil. The selection of the oil is therefore very important, according to the desired application. Oils with a high unsaturated fatty acid content allow an oxidizing polymerization with oxygen in the air. This treatment makes it possible to remove the water from the wood and to prevent further water uptake, and also makes it possible to improve the dimensional stability.

Robert H. White, in the document Flame Retardancy of Wood, pages 251 to 257, published in 1992 in Recent Advances in Flame Retardancy of Polymeric Materials Proceedings of $3^{rd}$ Annual BCC Conference on Flame Retardancy, 1992 May 19-21, Stamford, Conn. Norwalk, Conn.: Business Communications Company Inc.; 192: 250-257, describes, in the second paragraph on page 254, the joint use of ammonium sulphate, diammonium phosphate, borax and sodium fluoride for simultaneously obtaining flame retardancy and a preservative effect. The risk of release of phosphates and sulphates into the environment limits the value of this method.

Susan L. Levan, in Chemistry of Fire Retardancy, published in 1984 in Advances in Chemical Series 207, summarizes, on pages 563 to 564, properties of the various boron-based compounds and of their flame-retardant ability. Several compounds are mentioned, including boric acid and sodium tetraborate (borax). Borax inhibits flame advancement, but has little impact on "smouldering" or "glowing". On the other side, boric acid reduces "smouldering" and "glowing", but has little effect on flame propagation. These two compounds are therefore used together. A form commonly used as a flame-retardant product is polyboron.

The processes of the prior art which have made it possible to significantly improve the resistance of wood to bacterial, fungal or insecticidal agents or the flame-retardancy of wood, involve the incorporation of toxic chemical agents into the wood and their release, in particular when exposed to rain, which represents an attack on the environment in which such woods are placed.

The other processes, which implement the incorporation of bactericidal and/or fungicidal agents that are nontoxic or only slightly toxic, have in particular the drawback of rapid release of the protective agents, which are rapidly released into the environment and once again, the wood object treated is simultaneously rapidly weakened.

There existed therefore a need for polysaccharide-based solid materials which show good resistance to attack by bacteria and fungi and good flame retardancy and which are environmentally friendly.

There also existed a need for polysaccharide-based materials which show notable resistance to attack by bacteria and fungi and notable flame retardancy and which contain a limited amount of products that are not completely environmentally friendly.

There also existed a need for objects consisting at least partially of a polysaccharide-based solid material, which are stable in an aggressive environment and not liable to release agents that are environmentally toxic or toxic to their users.

SUMMARY

According to a general aspect, the disclosure relates to a polysaccharide-based solid material comprising, in its mass, at least one bactericidal and/or fungal and/or insecticidal and/or flame-retardant preserving agent selected from the group consisting of boron, boron derivatives, silica, silica derivatives, aluminum, aluminum derivatives, aluminosilicate derivatives, phosphorus, phosphorus derivatives, iodine, iodine derivatives, and mixtures of at least two of them; and at least one particular complexing agent complexed at least partially with the preserving agent and/or a polymeric matrix comprising a complexing agent for the preserving agent and which is capable of forming bonds with functions of the polysaccharides present.

This material exhibits a notable resistance to environmental attacks and is not toxic to the natural and human environment. Among the numerous applications, the materials obtained according to the invention can advantageously be used in the preparation of toys, outdoor furniture, wood for construction, decking for patios and utility wood (wooden posts on an electricity distribution network).

According to an aspect of the invention, there is provided a polysaccharide-based solid material comprising at least one active agent, wherein the active agent is selected from the group consisting of a bactericidal active agent, a fungicidal active agent, an insecticidal active agent, and a flame-retardant active agent;

and said active agent comprises, by weight, more than 50% of at least one compound selected from the group consisting of boron, boron derivatives, silica, silica derivatives, aluminum, aluminum derivatives, aluminosilicate derivatives, phosphorus, phosphorus derivatives, iodine, oxygenated iodine derivatives, and mixtures thereof, and at least one complexing agent at least partly complexing the active agent.

According to another aspect of the invention, there is provided a method for treating a polysaccharide based material, comprising:

preparing a solution of at least one bactericidal or fungicidal or insecticidal or flame-retardant active agent;

preparing a solution of at least one complexing agent of said active agent;

impregnating the polysaccharide based material by the solution of complexing agent;

impregnating the polysaccharide based material by the solution of active agent; and heating material after impregnating by the solution of complexing agent, before or after impregnating by the solution of active agent.

The following provides an outline of other possibly preferable and non-restrictive features of the invention, which will be more fully described hereinafter.

A first subject of the disclosure consists in particular of solid materials, which are preferably solid at ambient temperature, and which contain in their mass:

cavities or no cavity;

at least one bactericidal and/or fungal and/or insecticidal and/or flame-retardant active agent, said active agent consisting, by weight, of more than 50%, even more advantageously of more than 60%, more preferably of more than 90%, of at least one compound selected from the group consisting of boron, boron derivatives, silica, silica derivatives, aluminum, aluminum derivatives, aluminosilicate derivatives, phosphorus, phosphorus derivatives, iodine, oxygenated iodine derivatives, and mixtures of at least two of them; and at least one of the following compounds selected from the group consisting:

of complexing agents for boron and/or for silica and/or for aluminum and/or for phosphorus and/or for iodine, said complexing agents having at least one of the following characteristics:

of being at least partially bound to one of the bactericidal and/or fungal and/or insecticidal and/or flame-retardant compounds present in said polysaccharide-based solid material, of forming chemical bonds with functions of the polysaccharides present in said polysaccharide-based material; and chemical bonds with functions of a polymeric matrix when present in the cavities existing in the polysaccharide-based solid material; and of polymeric matrices comprising a complexing agent for boron and/or for silica and/or for aluminum and/or for phosphorus and/or for iodine, said polymeric matrices:

being capable of forming bonds with functions of the polysaccharides present in the polysaccharide-based material; and preferably having a size similar to or greater than that of the cavities present in the polysaccharide-based solid material.

According to a preferred embodiment, the polysaccharide-based solid materials according to the invention contain at least one boron-based or boron-derivative-based active agent; this agent is preferably selected from the group of oxygenated boron derivatives, such as borates.

According to another preferred embodiment, the polysaccharide-based solid materials according to the invention contain at least one silica-based or silica-derivative-based active agent; this agent is preferably selected from the group of oxygenated silicas, such as sodium silicate or silicic acid.

According to another preferred and advantageous embodiment, the polysaccharide-based solid materials according to the invention contain at least one aluminum-based or aluminum-derivative-based active agent; this agent is preferably selected from oxygenated aluminum derivatives such as sodium aluminate.

According to another preferred embodiment, the polysaccharide-based solid materials of the invention contain at least one active agent based on aluminosilicates such as sodium aluminosilicate and/or the tricalcium form of calcium aluminum silicate.

According to another preferred and advantageous embodiment, the polysaccharide-based solid materials according to the invention contain at least one active agent based on phosphorus or on a phosphorus derivative preferably selected from the group of oxygenated phosphorus derivatives, such as ammonium phosphate, diammonium phosphate, sodium phosphate and/or potassium phosphate.

According to another preferred embodiment, the polysaccharide-based solid materials of the invention contain at least one active agent based on iodine or on an oxygenated iodine derivative, such as potassium iodate and/or sodium iodate.

According to a variant of particular advantage, the active agent present in the polysaccharide-based materials of the invention is a mixture which contains less than 40% of a bactericidal and/or fungal and/or insecticidal and/or flame-retardant compound, which is water-soluble, preferably at ambient temperature. The active agent is then advantageously selected from the group consisting of acid copper chromate (ACC), ammoniacal copper arsenate (ACA), ammoniacal copper zinc arsenate (ACZA), chromated copper arsenate compounds (CCA type A, B and/or C), chromated zinc chloride (CZC), alkyl ammonium compounds (AACs) containing mainly didecyldimethyl ammonium chloride (DDAC minimum of 90%), quaternary ammoniacal copper (ACQ type A, B, C and/or D), copper bis(dimethyldithiocarbamate) (CDDC), ammoniacal copper citrate (CC), copper azole (CA) type A (CBA-A), copper azole type B (CA-B), copper HDO type A (CX-A) where the HDO is bis(N-cyclohexyldiazeniumdioxy), and mixtures of at least two thereof; the active agent is preferably selected from the group consisting of the water-soluble preserving agents listed in the "Book of Standards 2006" of the AWPA, section P5-06, pages 111 to 116, ISSN 1534-195X, which is incorporated into the present application by way of reference.

According to a preferred and advantageous embodiment of the invention, the total amount of active compound and of complexing agent and/or of polymeric matrix present in said polysaccharide-based material represents, by weight, at least 0.1%, preferably at least 1%, more preferably from 5% to 30% of said polysaccharide-based material. This amount varies substantially according to the type of wood used. Thus, for a post of grey pine, the value may be 7% by weight of active compound and of complexing agent and/or of polymeric matrix relative to the total weight of a treated post. On the other hand, for a post of yellow pine, the value may be 22% by weight of active compound and of complexing agent and/or of polymeric matrix relative to the total weight of a treated post.

According to another advantageous variant, at least 1%, preferably at least 25%, more preferably at least 50% of the complexing agent is bound to one of the bactericidal and/or fungal and/or insecticidal and/or flame-retardant compounds present in said polysaccharide-based solid material.

According to another variant of particular advantage, at least 1%, preferably at least 25%, more preferably at least 50% of said complexing agent forms chemical bonds with chemical functions of the polysaccharides present in said polysaccharide-based material.

According to another advantageous embodiment of the invention, at least 1%, preferably at least 25%, more preferably at least 50% of said complexing agent forms chemical bonds with functions of the polymeric matrix present in the cavities existing in the polysaccharide-based solid material.

According to another particular advantage, more than 80%, preferably more than 90% of the polymeric matrices present in the polysaccharide-based material have no bond with the functions of the polysaccharides present in the polysaccharide-based material.

Advantageously, the size of the matrices may be similar to or greater than that of the cavities present in the polysaccharide-based solid material.

A preferred subgroup of polysaccharide-based solid materials of the invention consists of the polysaccharide-based solid materials comprising at least one polymeric matrix containing no complexing agent.

Another advantageous subgroup consists of the polysaccharide-based solid materials comprising a polymeric matrix, and in which the boron and/or silica and/or aluminum and/or phosphorus and/or iodine atoms and/or the functions containing boron and/or the functions containing silica and/or the functions containing aluminum and/or the functions containing phosphorus and/or the functions containing iodine, present in the polysaccharide-based solid material, are at least partially bound to the complexing agent present in the polymeric matrix and/or at least partially bound to at least one function of the polymeric matrix.

Another subgroup of particular advantage consists of the polysaccharide-based solid materials in which the boron and/or silica and/or aluminum and/or phosphorus and/or iodine atoms present in said polysaccharide-based solid material have, at least partially, chemical interactions with one of the complexing agents present.

Advantageously, the boron and/or silica and/or aluminum and/or phosphorus and/or iodine atoms present in said polysaccharide-based material form, at least partially, coordination bonds with one of the complexing agents present.

According to an advantageous embodiment of the invention, the amount of active agent present per $m^3$ of polysaccharide-based material corresponds to a silica and/or aluminum and/or phosphorus and/or iodine equivalent of greater than 0.1 $kg/m^3$; preferably this amount is greater than 0.2 $kg/m^3$, more preferably this amount is between 0.5 and 30 $kg/m^3$, it preferably ranges from 1 to 15 $kg/m^3$, and more advantageously it ranges from 2 to 10 $kg/m^3$, more advantageously it is approximately 5 $kg/m^3$.

Preferably, the amount of complexing agent, present in the polysaccharide-based material, is greater than 0.5, preferably greater than 1 mol per mole of boron and/or of silica and/or of aluminum and/or of phosphorus and/or of iodine present; preferably, this amount is between 1 and 10 mol, more preferably this amount is between 1 and 5 mol, more advantageously it is approximately 2 mol of chelating agent per mole of boron and/or of silica and/or of aluminum and/or of phosphorus and/or of iodine present in the polysaccharide-based material.

Advantageously, the cavities existing in the polysaccharide-based solid material have a volume which ranges from $5\times10^{-5}$ $mm^3$ to $2\times10^{-2}$ $mm^3$ and the amount of polymeric matrix present is greater than 1 $kg/m^3$, preferably this amount ranges from 5 to 30 $kg/m^3$, even more preferably it is approximately 16 $kg/m^3$ of the polysaccharide-based material.

According to an embodiment of the invention that is of particular advantage, the complexing agent for boron and/or for silica and/or for aluminum and/or for phosphorus and/or for iodine is, when it is present, selected from the group of chemical compounds comprising hydroxyl and/or amine and/or carboxylic acid functions.

Advantageously, the complexing agent for boron is selected from the group of chemical compounds comprising hydroxyl and/or amine and/or carboxylic acid functions, such as an acetic acid function, or more preferably from the group consisting of polyamines, polyols, polyolamines and mixtures of at least two thereof. Advantageously, the amine functions are of primary or secondary type and the polyol functions are of diol type, more preferably of vicinal diol type, the polyols advantageously containing from 2 to 7 carbon atoms in the chain. The complexing agent for boron is preferably selected from the group consisting of N-methyl-D-glucamine (NMG), tris(hydroxymethyl)aminomethane (THAM), 1,3-bis[tris(hydroxymethyl)methylamino]propane, (hydroxyethyl)amine, di(hydroxyethyl)amine, iminodicarboxylic acids such as iminodicarboxylic acid, iminodiacetic acid and mixtures of at least two thereof.

Preferably, the complexing agent for boron and/or for silica and/or for aluminum and/or for phosphorus and/or for iodine, capable of forming chemical bonds with functions of the polysaccharides, is selected from the group consisting of the chelating agents described in the previous two paragraphs, in relation to the nature of the atom to be complexed, and which comprise a chemical function that can react on hydroxyl and/or methoxy functions present in the polysaccharide components of the polysaccharide-based material; such additional functions are preferably halogenated or epoxide functions; more preferably, the complexing agent for boron, capable of forming chemical bonds with functions of the polysaccharides, is selected from the group consisting of epichlorohydrin, polyethylene glycol diglycidyl ethers, the molecules of formula $Cl-CH_2CH(OH)-N(CH_3)-(CHOH)_5-CH_2OH$ or $Cl-CH_2CH(OH)-NH-C-(CHOH)_3$, and mixtures of at least two thereof.

Another subgroup of polysaccharide-based solid materials according to the invention and of particular advantage is characterized in that the polymeric matrix to which the complexing agent is grafted has a size less than that of cavities present in the polysaccharide-based material and it is selected from the group consisting of epoxy resins, polyethers, polyvinyl alcohols, polyurethanes, nylons, polyacrylates, and mixtures of at least two thereof; preferably, the polymeric matrix is selected from the group consisting of the polymers obtained by polymerization of a water-soluble monomer containing said complexing agent, it is more preferably a monomer obtained by reaction of a glycidyl methacrylate and of N-methyl-D-glucamine (NMG) in order to produce (N-glucidol-N-methyl)-2-hydroxypropyl methacrylate (GMHP).

The epoxy matrix is preferably obtained by in-situ crosslinking of a polyethylene glycol diglycidyl ether, in the presence of amine and/or hydroxyl functions, preferably in the presence of diamines, and in the presence of at least one chelating agent containing a primary or secondary amine which is preferably NMG, THAM or a mixture thereof. The matrix is advantageously selected from the group consisting of polyacrylates, preferably from the group of poly(alkyl acrylate)s which are at least partially water-soluble and which contain the chelating agent in the form of a monomer: (N-glucidol-N-methyl)-2-hydroxypropyl methacrylate (GMHP).

The polyethers are advantageously obtained:
from at least one polyethylene glycol divinyl ether that is at least partially water-soluble and by crosslinking using a cationic initiator in the presence of at least one chelating agent preferably selected from the group of chelating agents having a vinyl ether function; or
by crosslinking of polyethylene glycol acrylate or dimethacrylate of average molecular mass in the region of or less than 1000 g/mol, in the presence of a thermal initiator and, preferably, also in the presence of at least one chelating agent having an acrylate and/or methacrylate function.

Another preferred subgroup of the polysaccharide-based solid materials according to the invention consists of the solid materials in which the polymeric matrix, capable of forming bonds with the functions of the material and having a size which allows it to be inserted into the cavities of the polysaccharide-based material, is selected from the group consisting of epoxy resins, polyethers, polyvinyl alcohols, polyurethanes, nylons, and mixtures of at least 2 thereat preferably, the polymeric matrix is selected from the group consisting of epoxy resins that are soluble in a solvent which is preferably an aqueous solvent, and/or of polyethers that are soluble in a solvent, preferably in an aqueous solvent; even more preferably, it is a polymeric matrix consisting of an epoxy resin obtained using a water-soluble polyether, even more advantageously it is an epoxy resin prepared using a chelating agent having amine and hydroxyl functions and using a water-soluble molecule containing more than one glycidyl ether (GE) function, such as polyethylene glycol diglycidyl ethers, preferably the polyethylene glycol diglycidyl ether with an average molecular weight of the order of 526 g/mol.

Advantageously, the polysaccharide-based solid materials of the invention comprise at least 1%, preferably at least 50%, even more advantageously at least 80% by weight of polysaccharides.

Preferably, in the polysaccharide-based solid materials of the invention, between 10% and 100% of the polysaccharides present have an average molecular weight of between 1000 and 1,000,000 g/mol, more preferably approximately 45% of the polysaccharides present have a molecular weight of between 200,000 and 600,000 g/mol.

More preferably, in the polysaccharide-based solid materials of the invention, the polysaccharides are selected from the group consisting of: hemicelluloses, celluloses, chemically modified celluloses, physically modified celluloses, chemically and physically modified celluloses, natural starches, chemically modified starches, physically modified starches, chemically and physically modified starches, and also mixtures of at least 2 thereof.

More advantageously, the polysaccharide-based solid materials according to the invention comprise, by weight:
from 1% to 150%, preferably between 15% and 40%, even more preferably between 20% and 30% of water;
from 26% to 34%, even more preferably approximately 29% of lignin;
from 16% to 22%, even more preferably approximately 18% of hemicellulose; and
from 37% to 61%, even more preferably approximately 45% of cellulose,
the % being expressed relative to the weight of the polysaccharide-based solid material when it is in its anhydrous form.

The polysaccharide-based solid materials of the invention are advantageously based on a wood which is preferably selected from the group of conifers, and more preferably from the group consisting of cedars (including American arborvitae and Western arborvitae), twisted pines (including Murray pine), yellow pines (including ponderosa pine), grey pines, red pines, white pines, silver pines, Northern pitch pines, Scots pines, Douglas firs, Canada hemlock and Western hemlock.

One subgroup of polysaccharide-based solid material, according to the invention and of particular advantage, is characterized in that the amount of unleached bactericidal and/or fungicidal and/or insecticidal and/or flame-retardant compounds present in the polysaccharide-based solid material, measured in a leaching test carried out according to the standard method for determining leaching E11-06 of the AWPA and for a normal test period of 14 days, is increased, preferably by at least 1%, even more preferably by at least 10%, and even more advantageously by at least 20%.

A second subject of the present disclosure relates to processes for impregnating a polysaccharide-based material having a solids content of greater than 20%. These processes comprise at least the following steps:
scratching the polysaccharide-based material when it is wood, this step therefore being optional;
reducing the relative moisture content of the polysaccharide-based material to a value, measured according to ASTM standard D4442, which is less than 95%, preferably between 15% and 30%, and more preferably approximately 20%;
impregnating the polysaccharide-based material using a chemical agent having at least one of the following abilities:
to form chemical bonds with functions of the polysaccharide-based material;
to be inserted into the cavities (cells) existing in the polysaccharide-based material;
to fix boron or one of its derivatives and/or silica or one of its derivatives and/or aluminum or one of its derivatives and/or phosphorus or one of its derivatives and/or iodine or one of its derivatives; and
to delay the release of boron and/or of silica and/or of aluminum and/or of phosphorus and/or of iodine in the presence of exposure to water;
and
impregnating the polysaccharide-based material using a solution based on boron and/or on silica and/or on aluminum and/or on phosphorus and/or on iodine.

According to a first variant of the second subject, the processes for impregnating a polysaccharide-based material, having a solids content of greater than 20% and which comprises cavities, comprise at least the following steps:
scratching the polysaccharide-based material when it is wood (optional step);
reducing the relative moisture content of the polysaccharide-based material to a value of between 15% and 35%;
fixing a complexing molecule for boron and its derivatives and/or for silica and/or for aluminum and/or for phosphorus and/or for iodine, to the walls of the cells of the polysaccharide-based material; and
impregnating the modified polysaccharide-based material obtained in the previous step using a solution based on boron and/or on silica and/or on aluminum and/or on phosphorus and/or on iodine.

According to a second variant of the second subject, the processes for impregnating a polysaccharide-based material, having at least 20% solids and which comprises cavities, comprise at least the following steps:
scratching the polysaccharide-based material when it is wood (optional step);
reducing the relative moisture content of the polysaccharide-based material to a value of between 15% and 35%;

inserting, into the cells of the polysaccharide-based material, a polymeric matrix into which a complexing molecule for boron and/or for silica and/or for aluminum and/or for phosphorus is incorporated; and impregnating the polysaccharide-based material, after the treatment of the previous insertion step, using a solution based on boron and/or on silica and/or on aluminum and/or on phosphorus.

These processes are of particular advantage when they are applied to polysaccharide-based solid materials, and more particularly based on cellulose, panels of agglomerated particles, plywood or OSB (oriented strand board). The cellulose-based material is then advantageously wood, preferably a conifer, preferably red pine or grey pine.

A third subject comprises solutions for impregnating a polysaccharide-based material.

The solutions are obtained by:
dissolution, in an aqueous solution, of an amount of tris (hydroxymethyl)methylamine (THAM) and/or of NMG of between 0.05 M and 5 M;
addition of an excess of epichlorohydrin to the solution prepared in the previous step;
stirring of the solution obtained in the previous step; and
extraction of the excess epichlorohydrin using a solvent which is preferably of organic type.

The solutions thus obtained are of aqueous type and they are characterized in that they have a pH between 7 and 13, preferably between 8 and 12.

Preferably, the tris(hydroxymethyl)methylamine (THAM) and/or NMG is (are) dissolved in an aqueous solution at least 80%, more preferably in water.

Advantageously, the amount of tris(hydroxylmethyl)methylamine (THAM) and/or of NMG dissolved is between 0.05 and 5 M, it is more advantageously between 0.2 and 1 M.

Advantageously, the excess of epichlorohydrin used during the preparation of the impregnating solution can be up to 30%, even more advantageously, the molar excess is approximately 20% of epichlorohydrin. The excess is preferably obtained by the addition of approximately 0.12 mol (excess of 20%) of epichlorohydrin per 0.1 mol of NMG or of THAM (11.1 grams).

According to a specific embodiment of the third subject of the invention, the impregnating solution obtained in the step in which an excess of epichlorohydrin is added is stirred for one hour.

Advantageously, the stirring temperature is between 5 and 60° C., even more preferably between 10 and 50° C., even more advantageously this temperature corresponds to ambient temperature.

Preferably, the solvent used for the preparation of the impregnating solution is of organic type and it is selected from the group consisting of solvents which are water-insoluble and which can extract the molecule synthesized. It may thus be a halogenated solvent, and preferably dichloromethane.

Advantageously, the extraction is preferably carried out in at least 2 successive steps with a volume of organic solvent representing at most twice the volume of the solution obtained in the previous step.

The pH of the impregnating solutions of the invention thus obtained is advantageously between 8 and 13, more preferably approximately 10.

The impregnating solutions constituting the third subject of the present invention are particularly suitable for the treatment of polysaccharide-based materials in which the polysaccharide part is cellulose-based, and more preferably wood-based.

A preferred subgroup of impregnating solutions of the invention consists of the polysaccharide-based solutions (preferably cellulose-based, and more preferably woods) which comprise, by weight:
from 1% to 50%, preferably from 2% to 20%, more preferably from 5% to 15% of complexing agent;
from 40% to 99%, preferably from 80% to 95%, more preferably approximately 90% of water or of a water-based solution; and
less than 10% of impurities and/or of additives, the additives preferably being selected from the group consisting of "modifying" resins, reactive diluents, surfactants in order to facilitate impregnation or a buffer in order to stabilize the targeted area or "fillers", the additives preferably being selected from the group of aluminas or silicas.

A particular subgroup of impregnating solutions of the invention consists of the impregnating solutions in which the impurities are selected from the group consisting of the derivatives of the bonding molecule (epichlorohydrin, ethylene glycol, glycidyl ether, glycidyl methacrylate, diglycidyl ether, diglycidyl methacrylate, etc.) or of the by-products of the reaction between the bonding molecule and the complexing function which is preferably NMG, THAM or a mixture thereof.

A fourth subject comprises the polymeric matrices surrounded by the walls of the polysaccharide-based material and which incorporate boron. These matrices are obtained in the polysaccharide-based material by the implementation of at least the following steps:
a) solubilization of the monomers, the crosslinking agent and the chelating molecule;
b) conditioning (optional) of the polysaccharide-based material, in the case of wood, in particular by scratching and/or drying;
c) insertion of the treating solution into the cavities of the polysaccharide-based material (preferably after creation of a partial vacuum in the reactor in which the polysaccharide-based material to be treated is placed);
d) heating of the polysaccharide-based material, preferably at 60° C. for one hour, in order to crosslink the polymeric matrix; and
e) impregnation of the polysaccharide-based material after the treatment of the previous step, using a solution based on boron and/or on silica and/or on aluminum and/or on phosphorus and/or on iodine.

According to a preferred embodiment, the polymeric matrices of the invention incorporate boron and/or silica and/or aluminum and/or phosphorus as preserving agent, and they are characterized by the presence of at least one chelating agent, grafted onto said polymeric matrix, in an amount representing from 1% to 80% by mass of the polymeric matrix, preferably from 2% to 20% by mass, and more preferably approximately 10% by mass; the preserving agent based on boron, on silica, on phosphorus or on aluminum represents from 1% to 80% by mass of the polymeric matrix, preferably from 2% to 20% by mass, and more advantageously it is in a molar ratio of 2:1 of chelating agent relative to preserving agent.

A fifth subject comprises the processes for treating a polysaccharide-based material which comprise the steps:
a) of impregnating said material using at least one solution as defined in the third subject of the present invention, at a pH of between 8 and 13, and which is preferably in the region of 10 and preferably regulated using NaOH;
b) of heating the impregnated material from the previous step at a temperature of between 40 and 105° C., preferably at a temperature of between 50 and 80° C., more preferably at a temperature of approximately 60° C., for a period of preferably between 15 minutes and 24 hours, more preferably between 30 minutes and 1 hour; and c) of impregnating the heated material obtained in the previous step using a solution of a compound selected from the group consisting of boric acid, sodium octaborate tetrahydrate (DOT), phosphorous acid, ammonium phosphate, sodium phosphate, and mixtures of at least 2 thereof, said solution having a concentration which makes it possible to obtain a molar ratio of the complexing agent to the boron molecule ranging between 0.1 and 2.0, preferably between 0.2 and 1.0, and more advantageously a molar ratio of boric acid to complexing agent of approximately 0.5.

Preferably, steps a) and c) are carried out simultaneously and are followed by step b).

According to a variant of the fifth subject, the processes for treating a polysaccharide-based material comprise the steps:

a') of preparing an impregnating solution which contains the compound of formula $ClCH_2CH(OH)CH_2NHC(CHOH)_3$ by:
- dissolution of 0.05 to 0.50 mol, preferably of 0.1 mol (12.112 grams) of THAM in 50 to 500 ml, preferably in 125 ml of water,
- addition of 0.06 to 0.60 mol, preferably of 0.12 mol (excess of 20%) of epichlorohydrin (11.1 grams),
- stirring of the solution obtained in the previous step, preferably for one hour and advantageously at ambient temperature,
- extraction of the solution (optional) obtained in the previous stirring step, using $CH_2Cl_2$ in a volume corresponding at most to twice the volume of the solution to be extracted, the extraction preferably being carried out with between 10 and 100 ml, even more advantageously with approximately 50 ml of $CH_2Cl_2$, in order to remove the excess epichlorohydrin which has not reacted;

b') of impregnating the polysaccharide-based material with the impregnating solution obtained in the previous step at a pH of between 7 and 13, preferably between 8 and 12, more preferably at a pH of 10, the pH being adjusted by the addition of the required amount (0.8 ml) of NaOH (50%); the insertion into the samples of wood advantageously being carried out under partial vacuum, more preferably at a partial vacuum of −65 cmHg;

c') of heating at between 50 and 70° C., preferably at 60° C. for a reaction lasting 0.5 to 24 hours, preferably for 18 hours; and d') of impregnating the polysaccharide-based material thus modified with an approximately 0.33 M (2% by mass) aqueous solution of boric acid, the pH of which has gone from 4.68 to 10 through the addition of 4.58 ml of NaOH (50%); the insertion into the samples of wood advantageously being carried out under partial vacuum, more preferably at a partial vacuum of −65 cmHg.

Preferably, steps b') and d') are carried out simultaneously and are followed by step c').

According to an advantageous embodiment of the present invention, in treatment step a'), the solution is preferably prepared in water and contains:
- from 0.2% to 2.5%, preferably approximately 1.2% of $H_3BO_3$;
- from 10% to 40%, preferably approximately 20% of GMHP in solution; and
- from 0.1% to 2.5%, preferably approximately 1% of a thermoinitiator, which is advantageously VA-060.

According to a particularly advantageous embodiment of the invention, the impregnating solutions of the invention are applied at a rate of at least 5 kg of treating solution, preferably at least 15 kg of treating solution, even more advantageously at a rate of from 20 to 120 kg of solution thus prepared per total $m^3$ of wood to be treated.

This treatment is advantageously carried out periodically, preferably every 5 years, and repeated so as to prolong the lifetime of the polysaccharide-based material that is to be protected.

A sixth subject of the present disclosure consists of the objects containing at least one of the polysaccharide-based solid material as defined in the first subject of the present invention or as obtained by implementation of one of the processes defined in the second subject of the present invention.

The objects of the invention are advantageously prepared by machining, carving, compacting or moulding, and they are advantageously selected from the group of toys, outdoor furniture, wood for construction, decking for patio and utility wood.

These polysaccharide-based objects exhibit notable preservation properties, in particular in an outdoor environment and/or in a particularly aggressive environment, due to their particular stability in the presence of bacterial, fungal, insecticidal and/or flame-retardant agents. These exceptional properties are obtained without the incorporation, into the material constituting the objects, of chemical products which are toxic to the environment, or by the incorporation of reduced amounts of chemical products that are potentially damaging to the environment.

By way of nonlimiting examples, mention may be made of toys, outdoor furniture, wood for construction, utility wood and any object normally used in humid, tropical or subtropical environments, which are characterized by a high moisture content favourable to the particularly aggressive development of bacterial or fungal agents.

BRIEF DESCRIPTION OF THE DRAWINGS

FIG. 5' is a graph illustrating the loss of boron as a function of time for a wood impregnated with an impregnating solution described in detail in Example 5'; the wood is subjected to a leaching test according to procedure E11-06 of the AWPA.

DETAILED DESCRIPTION OF THE PREFERRED IMPLEMENTATIONS

Figure 1:
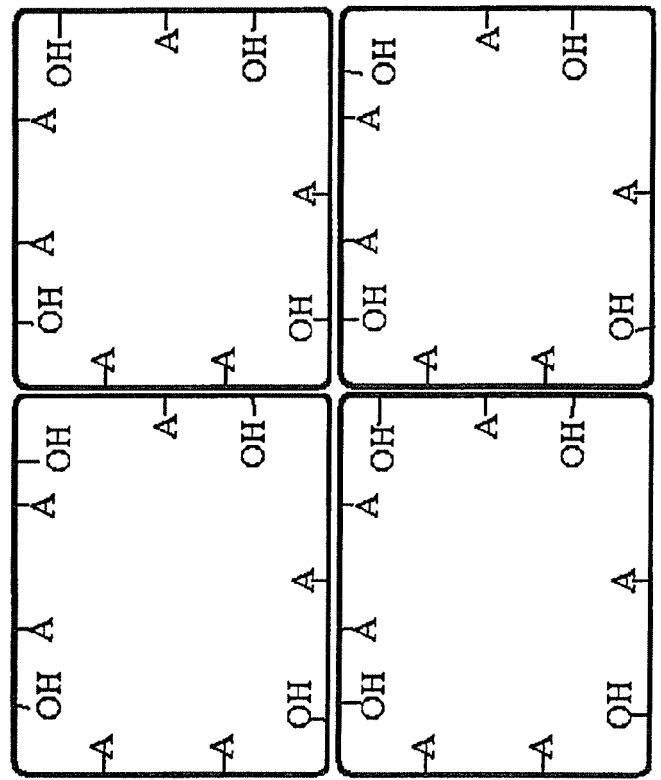
FIG. 1 shows cells of wood with the addition of chelating agents "A" for boron without being fixed to the cells of the wood.

In the context of the present disclosure, the definitions hereinafter are used.

Active agent or preserving agent: the term "protective compound" is used for a compound having at least one of the following properties: bactericide, fungicide, insecticide and flame-retardant. These protective compounds are advantageously selected from the group consisting of boron, boron derivatives (preferably oxygenated boron derivatives such as borates), silica, silica derivatives (preferably oxygenated silica derivatives), aluminum, aluminum derivatives (preferably oxygenated aluminum derivatives such as aluminas), aluminosilicate derivatives, phosphorus derivatives (preferably oxygenated phosphorus derivatives), iodine, oxygenated iodine derivatives, and mixtures of at least two thereof. Among the oxygenated boron derivatives, mention may be made of boric acid. Mention may also be made of sodium borates, sodium tetraborate, disodium octaborate tetrahydrate (DOT), sodium metaborate, ammonium pentaborate, potassium borate, potassium tetraborate, potassium pentaborate (see the company Rio Tinto Borax for a more exhaustive list: http://www.borax.com/).

Polysaccharides: these are woods, starches, guar gums, xanthan gums, celluloses, chitins, chitosans, glycans, galactans, glucans, hemicelluloses, pectins, mannans, dextrins; the preferred starches are potato starch, corn starch, wheat starch, tapioca starch, rice starch, waxy starches, barley starch, etc.; the preferred celluloses are carboxycelluloses, methoxyethylcelluloses, carboxymethylhydroxycelluloses, methylcelluloses, hydroxyethylcelluloses, etc. The polysaccharides considered are of natural origin, and are unmodified or modified by a chemical and/or physical treatment.

Polysaccharide-based solid materials: it is any material which contains a certain percentage of polysaccharides and is solid, preferably at ambient temperature. It may be, in a nonlimiting manner, wood, panels of agglomerated particles, plywood or OSB (oriented strand board).

The polysaccharide-based solid materials of the invention advantageously contain internal cavities, the wall of which consists mainly of carbohydrates and the size of which is advantageously less than $5 \times 10^{-2}$ mm$^3$, and more particularly between $5 \times 10^{-5}$ mm$^3$ and $2 \times 10^{-2}$ mm$^3$.

Epoxy resin: it is advantageously any water-soluble epoxy resin. Ethylene glycol diglycidyl ether (CAS: 2224-15-9), diethylene glycol diglycidyl ether (CAS: 4206-61-5), 1,4-butanediol diglycidyl ether (CAS: 2425-79-8) and polyethylene glycol diglycidyl ether (Mw=526) (CAS: 26403-72-5), all available from Sigma-Aldrich, are examples of potential candidates.

Complexing molecule: it generally contains hydroxyl functions on vicinal carbons or a high concentration of hydroxyl functions. The molecules selected also have an amine function. The presence of a high concentration of hydroxyl functions allows the complexation of borates, whereas the nitrogen atoms make it possible to stabilize these interactions by maintaining the "local" pH at an acceptable value in order to promote boron complexation.

"Curing" agent (hardener): their function is to ensure the polymerization of the reactive species. They can advantageously be chosen from: primary or secondary amines and polyamines, anhydrides, polyamides, alcohols, etc.; it is a question of selecting soluble molecules, which brings about a considerable simplification when the impregnating processes according to the invention are implemented.

The examples hereinafter, carried out on wood, are given merely by way of illustration and should not be interpreted as constituting any limitation of the invention.

By means of a chemical treatment of the wood, a complexing agent is introduced into the cells of the wood or fixed to the wood cells. Boric acid or disodium octaborate tetrahydrate (DOT) will be added to this agent in order to protect the wood against rotting or harmful insects. The use of a specific complexing agent makes it possible to considerably reduce leaching of the boric acid or disodium octaborate tetrahydrate (DOT) molecules and thus allows these wood-preserving agents to be used for outside applications.

FIGS. 1 to 4 represent a schematic sectional view of four different cells of the wood, in which the hydroxyl functions are represented by "OH". In these four figures, various conditions of interaction of the chelating agent "A", which is inserted into its walls, are described.

FIG. 1 shows the insertion of the chelating agent "A" into the cells of the wood, the chelating agent being capable of interacting with the fungicidal agent that will be added; however, the chelating agent is not bound to the walls of the cell nor to a polymeric matrix.

Figure 2:
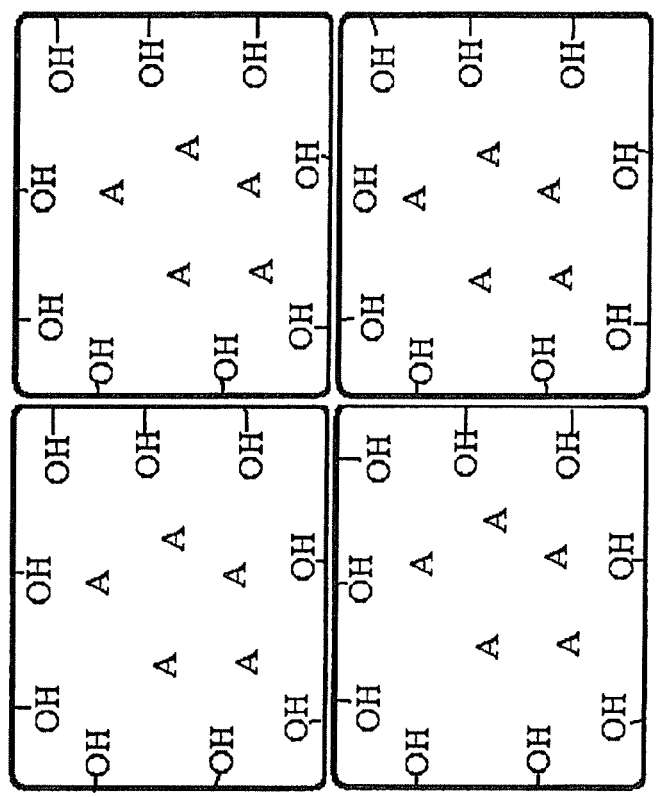
FIG. 2 shows cells of wood with the addition of chelating agents "A" for boron fixed to the walls of the wood.

In FIG. 2, the chelating agent is selected (or modified) so that it has a function which allows it to interact with the walls of the wood cells. The agent is therefore fixed to the walls and makes it possible to obtain better retaining of the fungal agents subsequently added. The degree of leaching is thus notably reduced.

Figure 3:
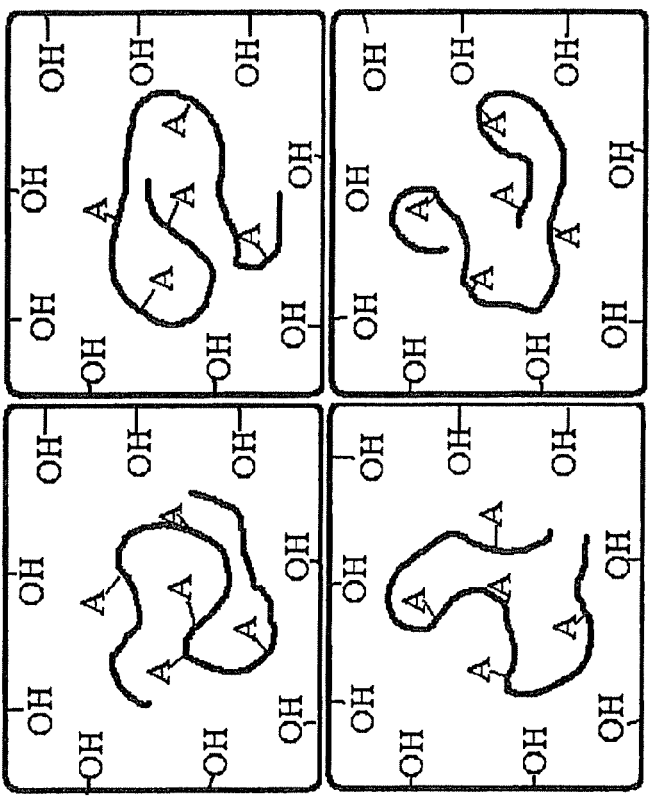
FIG. 3 shows cells of wood with the addition of chelating agents "A" for boron fixed to a polymeric matrix.

In FIG. 3, the chelating agent reacts with a polymeric matrix which is inserted into the wood cells. The various reagents are inserted in the form of monomers. Then, after impregnation, various molecules are reacted in order to form the polymeric matrix to which the chelating agent is fixed.

Figure 4:
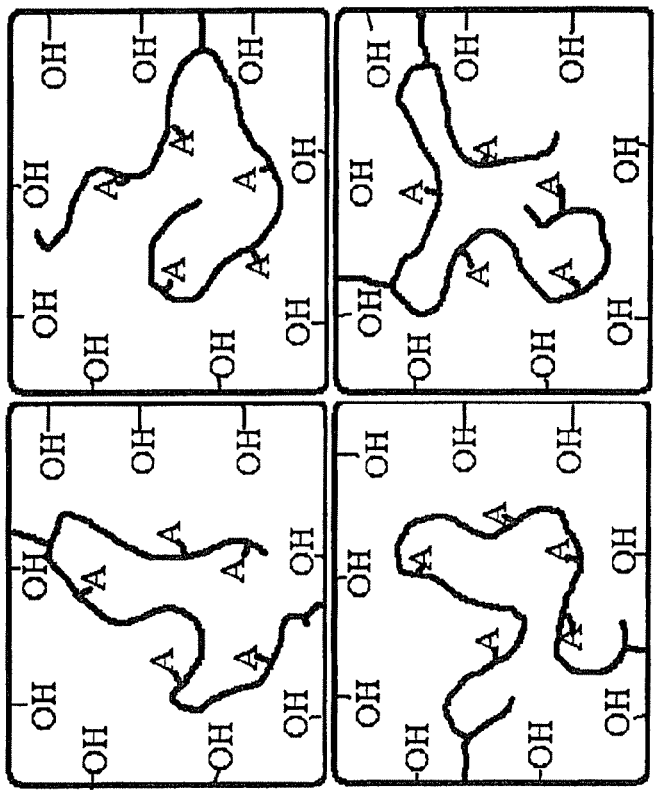
FIG. 4 shows cells of wood with the addition of chelating agents "A" for boron fixed to a polymeric matrix bound to the walls of the cells of the wood.

In FIG. 4, as in the case of FIG. 3, the chelating agent is fixed to the polymeric matrix. However, the choice of the various monomers is made in such a way that some of them have functions which can interact with the hydroxyl functions present on the walls of the cells.

Advantageously, the properties of the treated wood have been improved by implementation of the impregnating processes of the invention. Examples 1 to 4 illustrate two variants of the invention, i.e.: firstly, in Examples 1 and 2, the fixing of a complexing molecule directly on the walls of wood cells, and, secondly, in Examples 3 and 4, the preparation of a polymer matrix into which the complexing molecule is incorporated. This matrix is then subsequently synthesized "in-situ", in the cells of the wood, from the monomers.

Examples 1 and 2 are essentially the same. Only the choice of the "complexing" agent is changed.

Examples 1 and 2

In summary, we attempt to generate a molecule having complexing properties in order to retain boron and having a function that can react with the hydroxyl functions present on the wood cells. In the description, steps 1 to 5 are aimed at achieving this objective.

The complexing agent is currently selected in order to retain the boron molecules by generating hydrogen bridges between these two molecules. These molecules (NMC or THAM) also have a nitrogen molecule in order to more adequately retain the "active" boric acid or borax molecule. This is necessary in order to keep the complexing environment at alkaline pHs.

Details concerning the structure that these molecules should possess are described, inter alia, in these documents: J. Chem. Soc., Faraday Trans., 1998, vol. 94, 683-689 to p. 689 or on the Rohm & Haas site (www.rohmhaas.com/ionexchange/boron_print.htm) for the Amberlite IRA743 resin, which is a styrene resin with a methyl glucamine functionality:

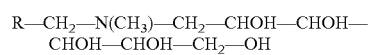

with R representing the polymeric matrix and the active group being essentially a weak base (tertiary amine) with a "sugar tail".

A structural formula is given below:

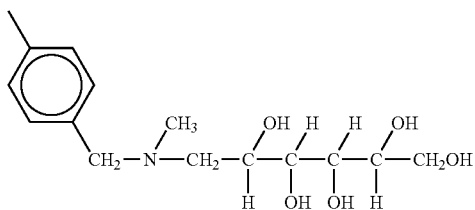

The assimilation of boron as borate $[B(OH)_4]^-$ is a complicated mechanism which results in the formation of a complex. Without being bound to this hypothesis, it is thought that the following representation is the final result:

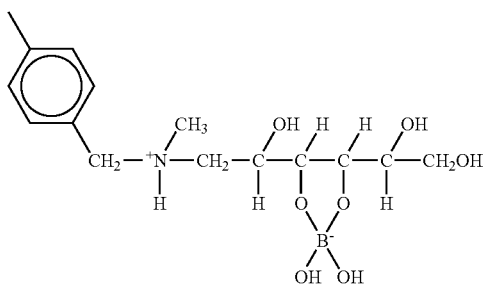

NMG (Example 1) and THAM (Example 2) are among the number of molecules which meet these criteria. An epichlorohydrin molecule will be reacted with these molecules. The aim is to add to the "complexing" molecule a function which makes it possible to graft it to the hydroxyl functions present on the walls of the wood cells. After the reaction, methylene chloride ($CH_2Cl_2$) is used in order to remove the traces of epichlorohydrin added in excess. At the end of these steps, the desired molecule is obtained, which molecule, firstly, effectively complexes the boron molecules and, secondly, grafts to the hydroxyl functions of the wood under appropriate pH conditions (presence of NaOH). An alkaline pH is necessary for the grafting reaction to take place.

The molecule inserted is heated to 60° C. in order to allow the reaction with the walls of the wood. The optimal conditions are not yet known, but we know that the reaction for fixing to the wood takes place in less than one hour. This step also makes it possible to evaporate the moisture content from the wood in order to allow the second impregnation step.

The second impregnation step contains an aqueous solution of boric acid at neutral or basic pH in order to allow adequate complexation of the boron.

Example 1

Grafting onto the Walls of the Wood Cells $1^{st}$ Step
1. 0.1 mol (19.5 g) of NMG is dissolved in 150 ml of water.
2. 0.12 mol (20% excess) of epichlorohydrin (11.1 g) is added, which makes it possible to graft the NMG onto the walls of the wood cells.
3. The mixture is stirred for one hour at ambient temperature.
4. The mixture is extracted twice with 50 ml of $CH_2Cl_2$ in order to remove the excess epichlorohydrin; this makes it possible to remove the epichlorohydrin but is not essential for successful synthesis.
5. The aqueous solution contains the following molecule:

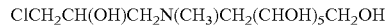

$ClCH_2CH(OH)CH_2N(CH_3)CH_2(CHOH)_5CH_2OH$

6. This molecule is rapidly impregnated into the wood at pH=10 (NaOH).

Steps 1 to 5 can be carried out with variants described in the Grinstead U.S. Pat. No. 4,755,298, the content of which is incorporated into the present application by way of reference.

The alkaline pH appeared to be necessary in order to allow the reaction of chlorine with the hydroxyl functions present on the walls of the wood. The wood samples, in the shape of cubes, consist of red pine sapwood, the moisture content of which is 9-10%.

wood-OH+Cl—R+NaOH→NaCl+$H_2O$+wood-O—R at 60° C.

7. The mixture is heated at 60° C. in order for the reaction to take place for 24 hours (grafting of the molecule+removal of water).

$2^{nd}$ Step
8. Boric acid (0.5 M) is impregnated under vacuum (−65 cmHg) at alkaline pH (pH=9).

The complexation of boron on the NMG functions is thus carried out.

The wood thus treated contains 2.0% by weight of boron and 1.9% by weight of complexing agent relative to the wood initially weighed. The measurements on resistance to leaching, carried out according to the modified AWPA procedure E1.1-06 (5 faces protected) gave a value of 37% loss of boron over a period of 8 days in the presence of the chelating agent versus 67% for a sample treated with boric acid without the addition of chelating agent.

Example 2

Grafting onto the Walls of the Wood Cells $1^{st}$ Step
1. 0.1 mol (12.1 g) of tris(hydroxymethyl)methylamine (THAM) is dissolved in 125 ml of water.
2. 0.12 mol (20% excess) of epichlorohydrin (11.1 g) is added.
3. The mixture is stirred for one hour at ambient temperature.
4. The mixture is extracted twice with 50 ml of $CH_2Cl_2$ in order to remove the excess epichlorohydrin.
5. The aqueous solution contains the following molecule:

$ClCH_2CH(OH)CH_2NHC(CHOH)_3$

6. This molecule will be rapidly impregnated into the wood at pH=10 (NaOH).
7. The mixture is heated at 60° C. in order for the reaction to take place, for 24 hours (grafting of the molecule+NaCl).

$2^{nd}$ Step
8. Boric acid (0.5 M) is impregnated under vacuum (−65 cmHg) at alkaline pH (pH=9).

Steps 1 to 5 can be carried out with variants described in the Grinstead patent bearing the number U.S. Pat. No. 4,755,298, the content of which is incorporated into the present application by way of reference.

The wood thus treated contains 2.7% by weight of boron and 3.3% by weight of complexing agent, relative to the weight of the wood initially weighed. The measurements on resistance to leaching, carried out according to the modified AWPA procedure E11-06 (5 faces protected), gave a value of 23% of loss of boron over a period of 15 days in the presence of chelating agent versus 32% for a sample treated with boric acid without the addition of chelating agent.

Examples 3, 3', 4 and 4'

These examples relate rather to the insertion of a polymer onto which the chelating function is grafted.

Example 3 summarizes the possibilities of inserting a polymer containing the chelating function into the wood cells. In these cases, a gel containing the chelating molecule, formed in-situ and inserted into the porous cells of the wood, after prior insertion of an epoxy resin and the boron atoms, is advantageously used.

In this example, an epoxy matrix is obtained by reacting an epoxy resin (molecule containing a reactive oxirane structure) with an amine-based, alcohol-based, anhydride-based, etc., curing agent.

In order to obtain an optimal epoxy, it is important to insert equivalent amounts of oxirane functions and of aminated protons. In the specific case of the example, a resin is selected, along with a commercial, water-soluble curing agent, and an appropriate amount of NMG will be added thereto.

By virtue of its amine function, the NMG has the ability to react with the resin in a manner similar to the molecules of the curing agent. A three-dimensional network is generated by the commercial epoxy, in which certain sites will be occupied by the active NMG molecule. The "effective" amount of NMG to be added to the solution is advantageously optimized.

More specifically, in this example, a first solution of resin and of boric acid is prepared and impregnated into the wood. After impregnation under vacuum, heating is carried out at 60° C. in order to remove the excess water.

This solution will subsequently be impregnated into the wood. The subsequent heating at 60° C. will allow the initiation of crosslinking, which should continue and be completed over the following days.

Details of Example 3 for Complexation of Boron onto a Polymeric Matrix Inserted into the Cells of Wood:
1. 210 g of poly(ethylene glycol)diglycidyl ether (Mw=526) and 12.4 g of boric acid are added to 100 ml of water. The sample is gently heated in order to facilitate dissolution of the boric acid.
2. This solution is subsequently impregnated into a cubic wood sample (19 mm×19 mm×19 mm) under vacuum and then dried at 60° C. overnight in order to remove the excess moisture.
3. 78 grams of NMG are diluted in 100 ml of water.
4. The wood is impregnated under vacuum.
5. Heating is carried out at 60° C. for 24 hours.
6. The NMG is reacted with the epoxy resin (grafting).

The epoxy resin reacts with the amine and hydroxyl functions of the NMG in order to form an epoxy-based network having boron-complexing functions.

Details of Example 3' for complexation of boron onto a polymeric matrix inserted into the cells of the wood. The insertion is carried out in a single step:
1. 7 g of $H_3BO_3$ (boric acid) are dissolved in 100 ml of water.
2. 31.6 g of NMG (N-methyl-D-glucamine) are added thereto.
3. After solubilization, 5 grams of EDA (ethylenediamine) are added.
4. After dissolution, 130 grams of PEGDGE (polyethylene glycol (400) diglycidyl ether) are added, and then mixed.
5. The wood is immediately impregnated under vacuum (−65 cmHg).
6. Heating is carried out at 60° C. for 24 hours.

The epoxy resin reacts with the amine and hydroxyl functions of the NMG and the amine functions of the EDA in order to form an epoxy-based network having functions for complexing boron in-situ in the polysaccharide-based matrix.

Example 4 is found to be a second example of this type of approach.

Briefly, in a first step, the aim is to graft a crosslinkable function onto the NMG molecule. Glycidyl methacrylate (GM) reacts at high temperature (70° C.) so as to become grafted to the NMG and thus form GMHP (3-(N-glucidol-N-methyl)-2-hydroxypropyl methacrylate).

Once this molecule has been obtained, this solution is diluted in water and it will be added to a thermal initiator ($Na_2S_2O_8$) and to a monomer with two acrylate functions (PEG400 diacrylate) in order to create a crosslinkable network.

After these solutions have been inserted into the wood and after said solutions have formed a crosslinked polymer in the cells of the wood, the wood is impregnated again with an aqueous solution of boric acid (2% by weight of boric acid in water) which complexes the NMG.

Details of Example 4—Complexation of Boron onto a Polymeric Matrix Inserted into the Cells of the Wood:
1. 9.75 g (50 mmol) of N-methyl-D-glucamine and 7.5 ml (55 mmol) of glycidyl methacrylate are added to 30 ml of 2-methylpyrrolidone. During this synthesis, n-methylpyrrolidone is used as solvent since glycidyl methacrylate (GM) is not water-soluble. The GM makes it possible to add a methacrylate function which will react with the thermal initiator in order to form the polymer with the NMG function.
2. The solution is mixed under a nitrogen atmosphere at 70° C. for 6 hours.
3. The mixture is allowed to cool.
4. 0.5 g of $Na_2S_2O_8$ and 1.01 g of PEG 400 diacrylate are added to 30 ml of water. The sodium persulphate plays the role of thermal initiator. It allows reaction of the methacrylate function on the molecule synthesized, and thus polymerization.
5. The two solutions are added to one another and are then impregnated into the wood (very rapid crosslinking: 2 minutes).
6. A solution of 2% by weight of boric acid in water is prepared and is then buffered at a pH of 10.3 using a concentrated NaOH solution. Soaking is allowed to take place for 3 hours under partial vacuum (−65 cmHg).

The wood thus treated contains 2.3% by weight of boron and 14.6% by weight of complexing agent, relative to the weight of wood initially weighed. The measurements on resistance to leaching, carried out according to the modified AWPA procedure E11-06 (5 faces protected), gave a value of 46% of loss of boron over a period of 8 days in the presence of the chelating agent versus 67% for a sample treated with boric acid without the addition of chelating agent.

Other variants of steps 1 and 2 of the process can be carried out using the publication by Bizak et al. (Macromol. Chem. Phys. 201, 2000, 577-584) as a basis.

Example 4' is found to be a second example of this type of approach. The treatment of the wood will, however, be carried out in a single step.

It is possible to obtain similar results using polymeric gels obtained with a monomer having an acrylate function. The preparation of this matrix is obtained by the method proposed by Bizak et al. The monomer is obtained by reacting glycidyl methacrylate (GM) with n-methylglucamine (NMG) in a molar ratio (11:10) where the GM is slightly in excess. The reaction, in order to prepare the monomer, is carried out in a solution of NMP (N-methylpyrrolidone) heated at 70° C. for 7 hours (or until the solution is soluble in water). 3-(N-glucidol-N-methyl)-2-hydroxypropyl methacrylate (GMHP) is thus obtained. The solvent (in this case NMP) may or may not be removed depending on the desired application. GMHP is a monomer which can crosslink in the presence, in particular, of a free-radical initiator (thermal or photon initiator) or through the presence of an electron beam (e-beam).

Once this molecule has been obtained, this solution is diluted in water and it will be added to a thermal initiator (for example, VA-060: 2,2'-azobis[2-[1-(2-hydroxyethyl)-2-imidazolin-2-yl]propane]dihydrochloride monohydrate from Wako Chemicals USA) in order to create a crosslinkable network. Other monomers comprising one or more acrylate functions can be added to this basic formulation in order to modify the properties of the gel formed.

Solution:
0.625 g of $H_3BO_3$;
25 ml of a solution of GMHP (such as the preparation described below); and
0.625 g of VA-060;
in 25 ml of $H_2O$.

The solution is inserted into the polysaccharide-based matrix by means of an impregnation into cubes of red pine sapwood (19 mm×19 mm×19 mm). The solution is impregnated under vacuum (−65 cmHg) for 30 minutes. The crosslinking is carried out by heating at 75° C. overnight under an inert atmosphere. It should be noted that the use of an inert gas is not necessary for samples of large size.

It involves a step for treatment of the wood in a single impregnation step followed by a crosslinking step. In this example, a thermal initiator is used by way of example, but it is possible to use other techniques known in the literature and used in order to crosslink the polymer by reacting an acrylate function.

Details of Example 4'—complexation of boron onto a polymeric matrix inserted into the cells of the wood:

1. 8.125 g (50 mmol) of N-methyl-D-glucamine and 6.25 ml (55 mmol) of glycidyl methacrylate are added to 25 ml of N-methylpyrrolidone. During this synthesis, n-methylpyrrolidone is used as solvent since the glycidyl methacrylate (GM) is not water-soluble. The GM makes it possible to add a methacrylate function which will react with the thermal initiator in order to form the polymer with the NMG function.
2. The solution is mixed under a nitrogen atmosphere at 70° C. for 6 hours.
3. Cooling is allowed to take place in 25 ml of water, 0.625 g of VA-060 is added. The VA-060 plays the role of thermal initiator. It allows reaction of the methacrylate function on the molecule synthesized and thus polymerization. 0.625 g of boric acid is added to this solution, followed by mixing.
4. 25 ml of the two solutions prepared are mixed together and then impregnated, in a single step, into cubes of wood of 19 mm×19 mm×19 mm consisting of red pine sapwood, using a partial vacuum (−65 cmHg).
5. The solution-impregnated wood is heated at 75° C. overnight under an inert atmosphere (nitrogen sweeping) in order to allow crosslinking of the polymeric matrix in the cells of the wood.

The wood thus treated contains 1.3% by weight of boron and 22% by weight of complexing agent (GMHP), relative to the weight of wood initially weighed. The measurements on resistance to leaching, carried out according to the AWPA procedure E11-06, gave a value of 45% of loss of boron over a period of 14 days in the presence of the chelating agent versus 100% for a sample treated with boric acid in the presence of non-crosslinked chelating agent (loss attained after less than 3 days for the latter case). A summary of the behaviour is given in FIG. 5.

The example is given by way of indication and does not limit the choice of components. By way of example, the impregnating solution can also contain at least one of the following elements:

an impregnating agent (in order to facilitate the impregnation of the solution into the cells of the wood);
a free-radical inhibitor (in order to stabilize the treating solution);
a UV-stabilizer (in order to prolong the useful life of the polymer prepared);
an antioxidant;
an oxygen scavenger;
a dye;
an ionic initiator; and
any other additive normally used in polymeric matrix formulations.

Other variants of steps 1 and 2 of the process can be carried out using the publication by Bizak et al. (Macromol. Chem. Phys. 201, 2000, 577-584) as a basis.

Examples 5 and 5'

Comparative Test

Example 5

Impregnation

Preparation of an Impregnating Solution which Contains the Compound of Formula $ClCH_2CH(OH)CH_2NHC(CHOH)_3$ by:

dissolution of 0.1 mol (12.112 g) of THAM in 125 ml of water,
addition of 0.12 mol (excess of 20%) of epichlorohydrin (11.1 g),
stirring of the solution thus obtained, for one hour, at ambient temperature; and
extraction of the solution obtained in the previous step by stirring, with a volume of 50 ml of $CH_2Cl_2$ in order to remove the excess epichlorohydrin that has not reacted.

Impregnation of a cube of wood (19 mm×19 mm×19 mm) with the impregnating solution obtained in the previous step, with adjustment of the pH to 10. The pH is adjusted by adding the required amount (0.8 ml) of NaOH (50%); at these concentrations, 3.17 mmol of the complexing agent will be fixed to the walls of the wood.

Heating of the blocks at 60° C. for 18 hours (for small blocks, the drying time is increased in order to accelerate the fixing treatment and water removal in order to facilitate the second impregnation).

Next, impregnation of the polysaccharide-based material thus modified with an aqueous solution of boric acid in order to insert 1.31 mmol in solution (2% by mass of boric acid); the pH has thus gone from 4.68 to 10 through the addition of 4.58 ml of NaOH (50%); the insertion into the wood samples is advantageously carried out under partial vacuum, more preferably at a partial vacuum of −65 cmHg.

Example 5'

Impregnation

Preparation of an Impregnating Solution which Contains GMHP as Described in Example 4':

1. 8.125 g (50 mmol) of N-methyl-D-glucamine and 6.25 ml (55 mmol) of glycidyl methacrylate are added to 25 ml of 2-methylpyrrolidone. During this synthesis, n-methylpyrrolidone is used as solvent since the glycidyl methacrylate (GM) is not water-soluble. The GM makes it possible to add a methacrylate function which will react with the thermal initiator in order to form the polymer with the NMG function.
2. The solution is mixed under a nitrogen atmosphere at 70° C. for 7 hours.
3. The solution is allowed to cool.
4. 0.625 g of VA-060 is added to 25 ml of water. The VA-060 plays the role of thermal initiator. It allows reaction of the methacrylate function on the molecule synthesized and thus polymerization.
5. 0.625 g of boric acid is added to this solution and then mixed:
   impregnation of a wood cube (19 mm×19 mm×19 mm) with the impregnating solution; the insertion into the wood samples is advantageously carried out under partial vacuum, more preferably at a partial vacuum of −65 cmHg; and
   heating of the blocks at 75° C. for 18 hours under a nitrogen atmosphere in order to dry the blocks and to allow crosslinking thereof.

Technique for Analysing the Amount of Boron that has Leached Out

Examples 5 and 5'

This technique is based on AWPA protocol E11-06. The blocks are soaked in demineralized water at ambient temperature. Water samples are taken regularly and an analysis by ICP spectrometry is carried out (after dilution of the solution by a factor of 250) in order to evaluate the amount of boron present in the solution. The results are represented in FIGS. 5 and 5'.

These results are compared with samples which are similar but in which the chelating agent was not crosslinked. These control samples underwent only the steps for impregnation of boron in the presence of the non-crosslinked chelating agent using the same solution.

Figure 5:
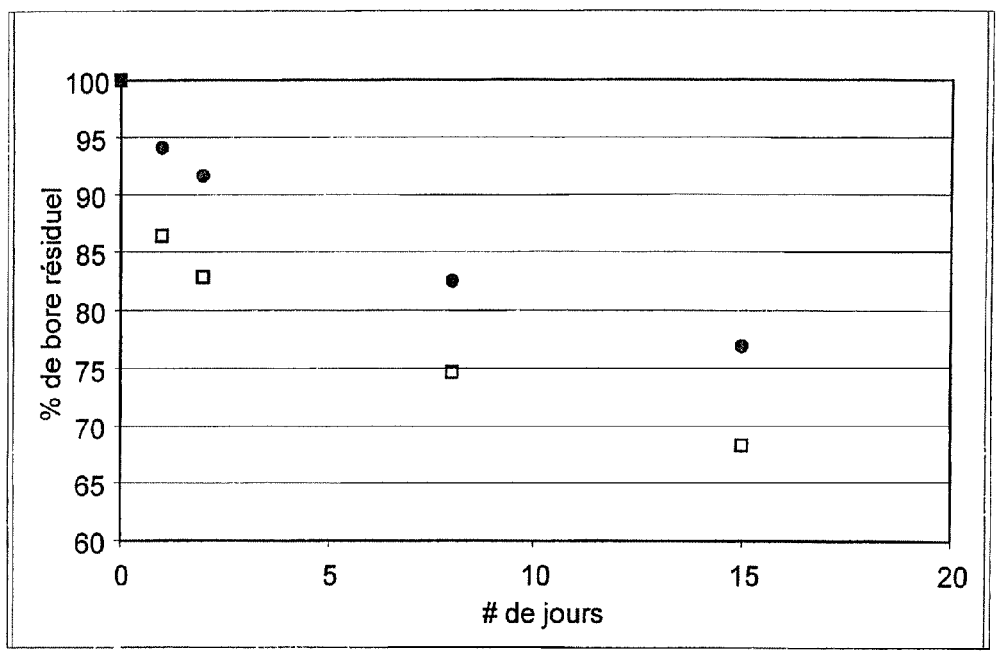
FIG. 5 is a graph illustrating the loss of boron as a function of time for a wood impregnated with an impregnating solution described in detail in Example 5; the wood, with which 5 faces of the cube are covered, is subjected to the leaching test according to procedure E11-06 of the AWPA.
Figure 5:
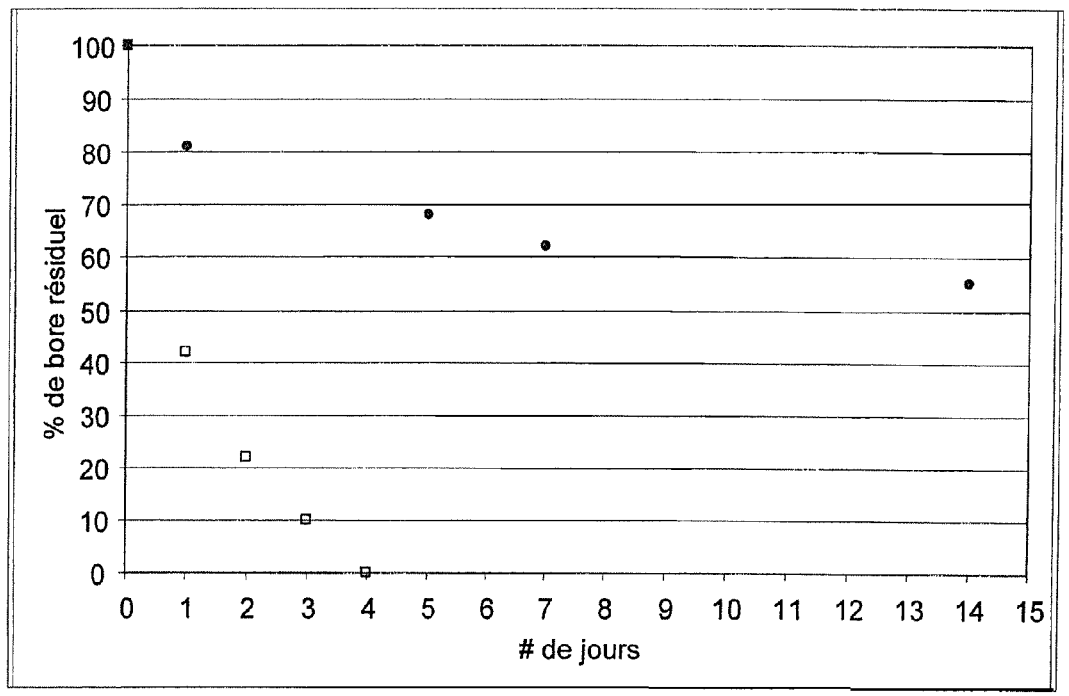

In FIG. 5, the samples of Example 5 (circles) were prepared according to the impregnating protocol of the invention as described in the procedure of Example 2.

It is therefore a sample of wood in the presence of boron and in the presence of a THAM-based chelating agent fixed by chemical modification of the wood. Furthermore, the reference samples (open squares) were prepared by following the same protocol, but eliminating the crosslinking step. It is therefore a sample of wood in the presence of boron and of chelating agent (control sample).

In FIG. 5', the samples of Example 5' (circles) were prepared according to the impregnating protocol of the invention as described in the procedure of Example 4'. It is therefore a sample of wood in the presence of boron and in the presence of an NMG-based chelating agent. Furthermore, the reference samples (open squares) were prepared by following the same protocol, but eliminating the crosslinking step. It is therefore a sample of wood in the presence of boron and of non-crosslinked chelating agent (control sample).

The comparison reported in FIG. 5' makes it possible to reveal a decrease in the degree of boron leaching of 45% after 14 days of soaking without using a protection of five surfaces of the samples prepared.

Example 6

Analysis of the Degree of Boron Retention

Tests for evaluating the degradation-resistance of the wood according to various treatments were carried out by following AWPA protocol E10-06. These tests were carried out using two brown rots: *Postia placenta* and *Gleophyllum trabeum*.

In order to correctly place the treatment of the present invention in context with respect to the treatment currently used in the industry, tests were also carried out for samples of wood treated with CCA or Cu-azole. The descriptive treatment of this invention, and which was used to protect the wood against fungal attacks, is similar to that of Example 3.

The gel is formed by the preparation of an epoxy. By way of comparison, two preparations were produced; one with boric acid as fungal agent (preparation 1), the other with disodium octaborate tetrahydrate (DOT) (preparation 2).

Preparation 1: 7 g of $H_3BO_3$ (boric acid) are dissolved in 100 ml of water; 31.6 g of NMG (N-methyl-D-glucamine) are added thereto after solubilization; 5 grams of EDA (ethylenediamine) are added; after dissolution, 130 g of PEGDGE (polyethylene glycol (400) diglycidyl ether) are added, followed by stirring.

This solution is immediately used for impregnation into the wood.

Preparation 2: 7 g of disodium octaborate tetrahydrate (DOT) are dissolved in 100 ml of water; 31.6 g of NMG (N-methyl-D-glucamine) are added thereto; after solubilization, 5 g of EDA (ethylenediamine) are added thereto; after dissolution, 130 g of PEGDGE (polyethylene glycol (400) diglycidyl ether) are added, followed by stirring.

This solution is immediately used for impregnation into the wood. It should be noted that the order for the addition of the constituents can be adjusted according to the preparation technique. This is merely one of the possible techniques.

These two preparations are used to treat blocks of 19 mm×19 mm×19 mm of red pine sapwood by means of a partial vacuum of −65 cmHg maintained for 30 minutes. This type of solution forms a gel in the cells of the wood after a period of one hour. In order to accelerate the crosslinking process and to allow drying, the blocks are heated overnight at 60° C.

In order to validate the capacity of our treatment to retain the boron in the wood and to play its role of wood-preserving agent, the treated blocks were soaked for one week in demineralized water in order to extract all traces of non-chelated boric acid or DOT.

After drying, the blocks were subjected to the laboratory "soil-block" culture test, strictly according to AWPA protocol E10-06.

Figure 6:
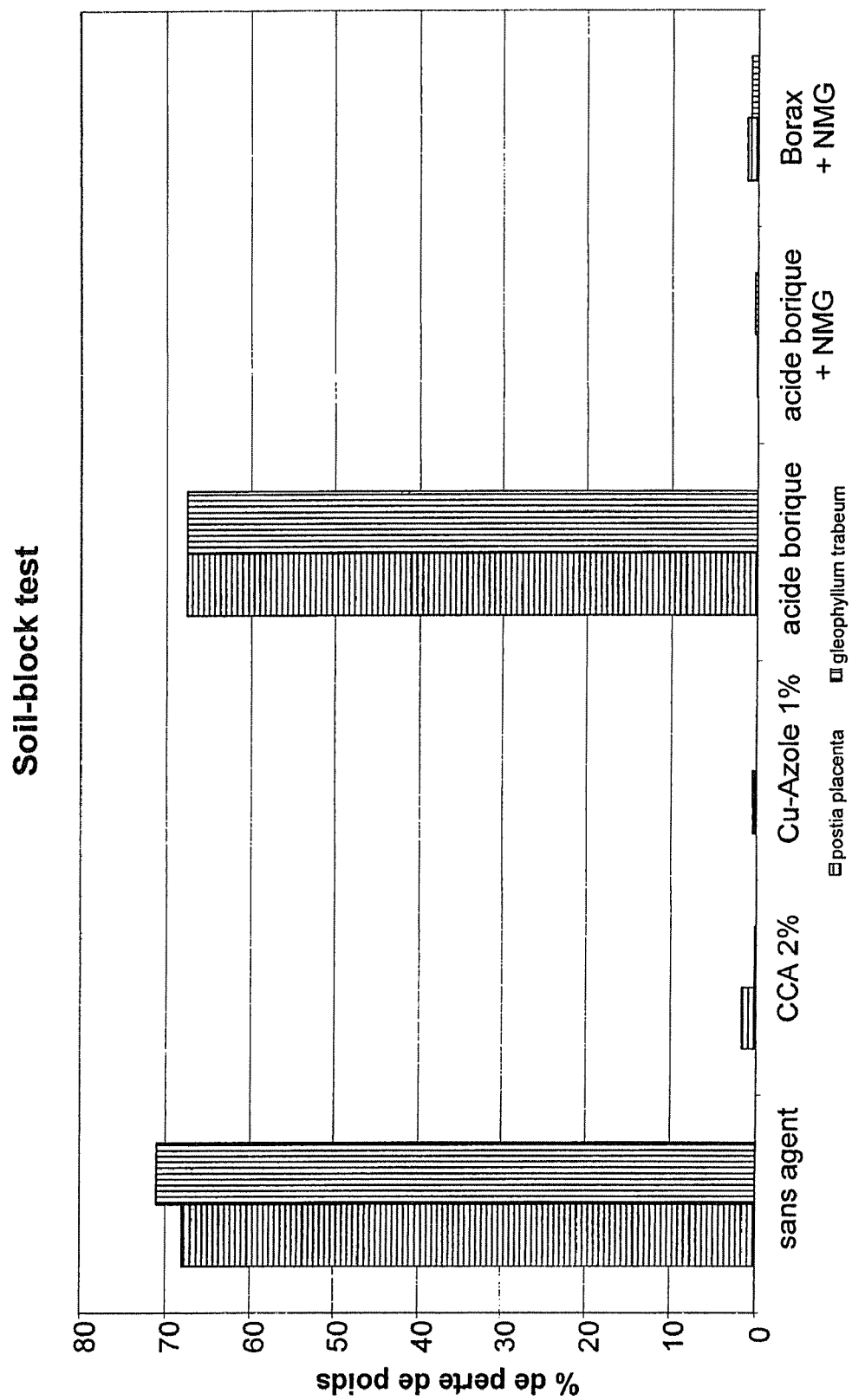
FIG. 6 is a graph illustrating the evaluation of the preservation efficiency on wood samples treated and then "leached" according to test E10-06 (soil-block test) carried out using cultures of the following brown rots: *Postia placenta* and *Gleophyllum trabeum*.

FIG. 6 summarizes the loss of weight (as percentage) after 20 weeks of exposure to degrading fungi of the blocks treated with various preserving agents (2% CCA, 1.04%$_{Cu}$ Cu-azole, 9 kg/m$^3$ boric acid, 15 kg/m$^3$ boric acid with the chelating agent (preparation 1) and 12 kg/m$^3$ borax with the chelating agent (preparation 2) obtained according to the method described in this example. The contents of boric acid and of DOT were adjusted so that there remains 8 kg/m$^3$ of these agents after the leaching treatment.

The results obtained after 20 weeks of test show a substantial loss for the nontreated samples and for the sample treated with boric acid without chelating agent, and having been leached. The results obtained for these configurations are very similar with regard to the degradation experienced and they demonstrate that, during leaching, the boric acid is not retained in the wood and does not therefore play its role in order to preserve the wood under these conditions.

As expected, the samples treated with CCA or copper-azole conserve their integrity and a very small fraction of wood is lost (losses less than 2% in all cases). A very similar result is obtained for the sample described in this invention. After considerable leaching of the treated samples, a substantial fraction of boron is retained (60-70% of the boron initially inserted, after analysis by ICP spectrometry). This clearly indicates that the chelating agent plays its role in retaining the boric acid. The values obtained are given in Table 1 (results of the weight losses of the wood blocks following a culture test according to AWPA protocol E10-06). The samples given in this table were subjected to leaching for one week before the E10-06 test.

TABLE 1

| Preserving agent | Weight loss (%) Postia placenta | Weight loss (%) Gleophyllum trabeum |
|---|---|---|
| no agent | 67.9 | 71 |
| 2% CCA | 1.6 | 0.2 |
| 1% Cu-azole | 0.49 | 0.06 |
| Boric acid | 67.5 | 67.5 |
| Boric acid + epoxy NMG | 0.12 | 0.33 |
| Tim-Bor (DOT) + epoxy NMG | 1.31 | 0.86 |

The analyses of degradation of the blocks treated with these two solutions demonstrate a resistance of the agents used in this invention that is equivalent to the commercial products (CCA and Cu-azole) for protecting the wood against attacks by brown rot. It can thus be concluded that, even if the chelating agent allows a considerable retention of boron-based compounds, the latter remain active for protecting the wood against attack by wood rot.

In conclusion, the tests carried out demonstrate that the polysaccharide-based solid materials of the invention, which comprise a complexing agent and/or a specific polymeric matrix, in addition to the preserving agent, have a lifetime which can be at least 50% longer than the lifetime of the same material containing only the preserving agent.

Although the present invention has been described using specific implementations, it is understood that several variations and modifications can be added to said implementations, and the present invention aims to cover such modifications, uses or adaptations of the present invention according, in general, to the principles of the invention and including any variation of the present description which will become known or conventional in the field of activity in which the present invention is situated, and which may apply to the elements mentioned above.

The invention claimed is:

1. A polysaccharide-based solid material comprising at least one active agent, wherein the active agent is selected from the group consisting of a bactericidal active agent, a fungicidal active agent, an insecticidal active agent, and a flame-retardant active agent;
   and said active agent comprises, by weight, more than 50% of at least one compound selected from the group consisting of boron, boron derivatives, silica, silica derivatives, aluminum, aluminum derivatives, aluminosilicate derivatives, phosphorus, phosphorus derivatives, iodine, oxygenated iodine derivatives, and mixtures thereof, and at least one complexing agent at least partly complexing the active agent
   wherein said material further comprises a polymeric matrix optionally forming bonds with functional groups of the polysaccharide,
   and,
   wherein the polymeric matrix is an epoxy matrix obtained by in-situ crosslinking of a polyethylene glycol diglycidyl ether in the presence of amine or hydroxyl functions.

2. A polysaccharide-based solid material comprising at least one active agent, wherein the active agent is selected from the group consisting of a bactericidal active agent, a fungicidal active agent, an insecticidal active agent, and a flame-retardant active agent;
   and said active agent comprises, by weight, more than 50% of at least one compound selected from the group consisting of boron, boron derivatives, silica, silica derivatives, aluminum, aluminum derivatives, aluminosilicate derivatives, phosphorus, phosphorus derivatives, iodine, oxygenated iodine derivatives, and mixtures thereof, and at least one complexing agent at least partly complexing the active agent
   wherein said material further comprises a polymeric matrix optionally forming bonds with functional groups of the polysaccharide,
   and,
   wherein the polymeric matrix is an epoxy matrix obtained by in-situ crosslinking of a polyethylene glycol diglycidyl ether in the presence of amine or hydroxyl functions, in the presence of diamines, and in presence of at least one chelating agent containing a primary or secondary amine which is NMG, THAM or a mixture thereof.

3. A method for treating a polysaccharide based material, comprising:
   preparing a solution of at least one bactericidal or fungicidal or insecticidal or flame-retardant active agent;
   preparing a solution of at least one complexing agent of said active agent;
   impregnating the polysaccharide based material by the solution of complexing agent;
   impregnating the polysaccharide based material by the solution of active agent; and
   heating said material after impregnating by the solution of complexing agent, and after impregnating by the solution of active agent,
   wherein impregnation by the solution of complexing agent and impregnation by the solution of active agent are carried out simultaneously,
   and wherein the active agent comprises boron or a boron compound, and the complexing agent of boron is selected from one of the groups consisting of:
   N-methyl-D-glucamine (NMG), tris(hydroxymethyl)aminomethane (THAM), 1,3-bistris(hydroxymethyl)methylamino]propane, (hydroxyethyl)amine, di(hydroxyethyl)amine, iminodicarboxylic acids, imino diacetic acid and mixtures thereof; and
   epichlorohydrin, polyethyleneglycol diglycidyl ethers, compounds of formula $Cl-CH_2CH(OH)-N(CH_3)-(CHOH)_5-CH_2OH$, $Cl-CH_2CH(OH)-NH-C-(CHOH)_3$ and mixtures thereof.

4. A method for treating a polysaccharide based material, comprising:
   preparing a solution of at least one bactericidal or fungicidal or insecticidal or flame-retardant active agent;
   preparing a solution of at least one complexing agent of said active agent;

impregnating the polysaccharide based material by the solution of complexing agent;
impregnating the polysaccharide based material by the solution of active agent; and
heating said material after impregnating by the solution of complexing agent, before or after impregnating by the solution of active agent,
wherein the solution of complexing agent contains the complexing agent in the form of a water-soluble monomer containing said complexing agent,
and wherein the monomer is a (N-glucidol-N-methyl)-2-hydroxypropyl methacrylate (GMHP) obtained by reaction of glycidyl methacrylate and the complexing agent N-methyl D-glucamine (NMG).

5. A method for treating a polysaccharide based material, comprising:
preparing a solution of at least one bactericidal or fungicidal or insecticidal or flame-retardant active agent;
preparing a solution of at least one complexing agent of said active agent;
impregnating the polysaccharide based material by the solution of complexing agent;
impregnating the polysaccharide based material by the solution of active agent; and
heating said material after impregnating by the solution of complexing agent, before or after impregnating by the solution of active agent,
wherein the solution of complexing agent contains a polyethylene diglycidylether, and the complexing agent has a primary or secondary amino group.

6. A method for treating a polysaccharide based material, comprising:
preparing a solution of at least one bactericidal or fungicidal or insecticidal or flame-retardant active agent;
preparing a solution of at least one complexing agent of said active agent;
impregnating the polysaccharide based material by the solution of complexing agent;
impregnating the polysaccharide based material by the solution of active agent; and
heating said material after impregnating by the solution of complexing agent, before or after impregnating by the solution of active agent,
wherein the solution of complexing agent contains the complexing agent in the form of (N-glucidol-N-methyl)-2-hydroxypropyl methacrylate (GMHP) and a polyalkylacrylate at least partly soluble in water.

7. A method for treating a polysaccharide based material, comprising:
preparing a solution of at least one bactericidal or fungicidal or insecticidal or flame-retardant active agent;
preparing a solution of at least one complexing agent of said active agent;
impregnating the polysaccharide based material by the solution of complexing agent;
impregnating the polysaccharide based material by the solution of active agent; and
heating said material after impregnating by the solution of complexing agent, and after impregnating by the solution of active agent,
wherein impregnation by the solution of complexing agent and impregnation by the solution of active agent are carried out simultaneously,
and wherein:
the solution of complexing agent is a solution which contains the compound of formula $ClCH_2CH(OH)CH_2NHC(CHOH)_3$, the pH of which is between 8 and 12, and which is obtained by:
dissolution of 0.05 to 0.50 mol of THAM in 50 to 500 ml of water,
addition of 0.06 to 0.60 mol of epichlorohydrin, and
stirring of the solution thus obtained, for one hour at ambient temperature,
the heating is carried out at between 50 and 70° C. for 0.5 to 24 hours; and
the solution of active agent is a 0.33 M aqueous solution of boric acid, the pH of which has gone from 4.68 to 10 through the addition of 4.58 ml of NaOH (50%); and
the impregnation is carried out under partial vacuum.

8. A method for treating a polysaccharide based material, comprising:
preparing a solution of at least one bactericidal or fungicidal or insecticidal or flame-retardant active agent;
preparing a solution of at least one complexing agent of said active agent;
impregnating the polysaccharide based material by the solution of complexing agent;
impregnating the polysaccharide based material by the solution of active agent; and
heating said material after impregnating by the solution of complexing agent, and after impregnating by the solution of active agent,
wherein impregnation by the solution of complexing agent and impregnation by the solution of active agent are carried out simultaneously,
and wherein the active agent and the complexing agent are in the same solution which contains:
from 0.2% to 2.5% of $H_3BO_3$;
from 10% to 40% of GMHP in solution; and
from 0.1% to 2.5% of a thermoinitiator.

* * * * *